US005231023A

United States Patent [19]

Morgan

[11] Patent Number: 5,231,023

[45] Date of Patent: Jul. 27, 1993

[54] RECOMBINANT MAREK'S DISEASE VIRUS

[75] Inventor: Robin W. Morgan, Landenberg, Pa.

[73] Assignee: Akzo N.V., Arnhem, Netherlands

[21] Appl. No.: 717,150

[22] Filed: Jun. 18, 1991

Related U.S. Application Data

[63] Continuation-in-part of Ser. No. 559,735, Jul. 30, 1990, abandoned.

[51] Int. Cl.[5] ...................... C12N 15/11; C12N 15/86; C12N 5/10

[52] U.S. Cl. .................................. 435/240.2; 424/88; 424/89; 424/93 A; 435/320.1; 536/23.1; 536/23.72

[58] Field of Search ............ 536/27; 435/320.1, 240.2, 435/235.1; 424/88, 93

[56] References Cited

FOREIGN PATENT DOCUMENTS

| | | |
|---|---|---|
| 0334530 | 9/1989 | European Pat. Off. . |
| WO8807088 | 9/1988 | PCT Int'l Appl. . |
| WO8901040 | 2/1989 | PCT Int'l Appl. . |

OTHER PUBLICATIONS

"Partial Transcription Map of Marek's Disease Herpesvirus in Lytically Infected Cells and Lymphoblastoid Cell Lines", Schatt et al., *International Journal of Cancer,* vol. 44, pp. 101-109 (1989).

"Structure of Marek's Disease Virus DNA: Detailed Restriction Enzyme Map", Fukuchi et al., *Journal of Virology,* Jul. 1984, pp. 102-109 USA.

"Gene Sequence and Mapping Data from Marek's Disease Virus and Herpesvirus of Turkeys: Implications for Herpesvirus Classification", Buckmaster et al. *Journal General Virology,* vol. 69, pp. 2033-2042 (1988) UK.

Journal of Virology, vol. 53:994-997 (1985) Fulcuchi et al.

Journal of General Virology, vol. 64:961-965 (1983) Ikuta et al.

Tomley et al., Molecular and Biochemical Parasitology, vol. 49, pp. 277-288, 1991.

Hnatow et al., Abstracts of the 64th Northeastern Conference on Avian Diseases, Jun. 1992, University Park, Pa., p. 3.

Bova et al., Virology, vol. 152, pp. 343-354, 1986.

Schwartz et al., Cell, vol. 32, pp. 853-869, 1983.

Yu et al., J. Gen. Virology, vol. 72, pp. 75-81, 1991.

Poulsen et al., Virus Genes, vol. 5, pp. 335-347, 1991.

Hudson et al. Nucl. Acids Res. vol. 14, pp. 5001-5012, 1986.

Claessens et al., J. Gen. Virol. vol. 72, pp. 2003-2006, 1991.

Noteborn et al., J. Virol. vol. 65, pp. 3131-3139, 1991.

Schnitzer et al., Virology, vol. 141, pp. 167-170, 1985.

Ross et al., J. Gen. Virol., vol. 72, pp. 949-954, 1991.

Binns et al. J. Gen. Virol., vol. 67, pp. 2825-2831, 1986.

Chambers et al. J. Gen. Virol. vol. 67, pp. 2685-2694, 1986.

Millar et al. J. Gen. Virol., vol. 67, pp. 1917-1927, 1986.

Cui et al. J. Virol., vol. 65, pp. 6509-6515 1991.

Chen et al. J. Virol., vol. 66, pp. 85-94, 1992.

Coussens et al. J. Virol. vol. 62, pp. 2372-2379 1988.

Ross et al. J. Gen. Virol., vol. 70, pp. 1789-1804, 1989.

*Primary Examiner*—Richard A. Schwartz
*Assistant Examiner*—David Guzo
*Attorney, Agent, or Firm*—Donna Bobrowicz

[57] ABSTRACT

The present invention relates to the use of Marek's Disease Virus Type I as a viral vector capable of expressing foreign genes in some poultry. Claimed are a nonessential insertion region on the DNA genome of the Virus; a plasmid comprising this region; a host cell containing the plasmid; and a vaccine comprising the recombinant virus.

13 Claims, 7 Drawing Sheets

FIG. 2A

```
                                         30                                      60
CAA CGT CGT ATC CGT ACC ATT GAT GCT GTT ATG TAT AAT TCC GTA GGT AGT ATT AGT TTT

                                         90                                     120
AGA GTC GTG TAC TTT CGA CGA AGA AAT GCC ACA TTC CAT CGT TTC TGC CTC CGG AGT CGA

                                        150                                     180
AGA CAT CCA GTC TAT TAC CTA GTT TTA ACC CTG TTT CAT ATT CTA CCA GAG TAT AAG ATT

                                        210                                     240
TGG AGA TCA GAC CGG CCC AGT TAT TAA CAA TAA AAA AGA TTA TTG GTG GAG GTG AAG ATG
                                                                             M

                                        270                                     300
GGT GTG TCC ATG ATA ACT ATA GTC ACA CTT CTA GAT GAA TGC GAT CGA TTG CCA GGA AGA
 G   V   S   M   I   T   I   V   T   L   L   D   E   C   D   R   L   P   G   R

                                        330                                     360
TCT AGA GAT GCT GCA TCT ACT TTA TGG ATA TTC CTT ATA AAG CAA TGT ATG GAA CAA ATA
 S   R   D   A   A   S   T   L   W   I   F   L   I   K   Q   C   M   E   Q   I

                                        390                                     420
CAG GAT GAT GTG GGT GTG CCC ATA ATC GCC AGA GCT GCA GAC CTA TTC CGT TTT GCC AAA
 Q   D   D   V   G   V   P   I   I   A   R   A   A   D   L   F   R   F   A   K

                                        450                                     480
CCC ATG TTA ATT CTT CCT CGG CAA CAT CGA CCG ATA GTA AGG ACA AAG CCA CCA GAT GGA
 P   M   L   I   L   P   R   Q   H   R   P   I   V   R   T   K   P   P   D   G

                                        510                                     540
ACT GGA GTT CGT GGT ACC GGA TTG GCC GGA ACT AGG GAT TCG TTT ATA GTG CGG CTA TTT
 T   G   V   R   G   T   G   L   A   G   T   R   D   S   F   I   V   R   L   F

                                        570                                     600
GAA GAT GTT GCA GGA TGT TCC ACA GAA TGG CAG GAT GTT CTA TCT GGA TAT TTG ATG TTG
 E   D   V   A   G   C   S   T   E   W   Q   D   V   L   S   G   Y   L   M   L
```

FIG. 2B

```
                                             630                                                 660
GAA TCT GAA GTT TCT GGT AAT GCT CCA CAT AGC TTG TGG ATA GTT GGG GCG GCA GAT ATA
 E   S   E   V   S   G   N   A   P   H   S   L   W   I   V   G   A   A   D   I

                                             690                                                 720
TGT CGC ATT GCG CTC GAA TGT ATT CCT TTG CCA AAA AGG TTA CTT GCA ATC AAA GTG TCT
 C   R   I   A   L   E   C   I   P   L   P   K   R   L   L   A   I   K   V   S

                                             750                                                 780
GGG ACC TGG TCC GGT ATG CCG TGG GCC ATT CCC GAC AAT ATT CAA ACT CTC TTG ACA TCT
 G   T   W   S   G   M   P   W   A   I   P   D   N   I   Q   T   L   L   T   S

                                             810                                                 840
ACA TGG GAA CCG AAG TTC GAC ACC CCA GAA GAT AGA GCG CAT TTT TGC GAC AGT GAT ATG
 T   W   E   P   K   F   D   T   P   E   D   R   A   H   F   C   D   S   D   M

                                             870                                                 900
GTA TGT GTA TAC AAA ATC CTC GGG TCC CCA CCC AAT CCT CTA AAA CCT CCG GAA ATC GAA
 V   C   V   Y   K   I   L   G   S   P   P   N   P   L   K   P   P   E   I   E

                                             930                                                 960
CCA CCT CAA ATG AGT AGT ACA CCC GGC AGA TTA TTC TGT TGT GGA AAA TGT TGC AAG AAA
 P   P   Q   M   S   S   T   P   G   R   L   F   C   C   G   K   C   C   K   K

                                             990                                                1020
GAA GAT AGA GAT GCG ATT GCA ATT CCG GTT CGT TAC ACT GCG ACA GGA AAG TCA CGA ATA
 E   D   R   D   A   I   A   I   P   V   R   Y   T   A   T   G   K   S   R   I

                                            1050                                                1080
CAG AAA AAA TGT AGA GCC GGT AGT CAT TAG CTG TTA TTC GAC AGA CCT ACT TGC TAC CAA
 Q   K   K   C   R   A   G   S   H   U

                                            1110                                                1140
TTA GAT ATA ATT ACA TGA TGG GGC GTA TAC ACA TTA CGA TTA GGT GCA TCG CTA CAA CCG

                                            1170                                                1200
TCG CTA TAG TGT CAC GTA TAA TTT GTA TAT TAG TGC AAT AAC AAA CCC TTC TAG ATC ACT

                                            1230                                                1260
TAT GTA TCC AGG CTA TCT TCC ATA TAC TTC TAA CAT CAG GAG AGA TTC AAC AAT CGA GCG

                                            1290
CAT TTG AAA GAC AAC GAT GAG CAG AGT CAA TGC TAC AAT GTT CGA TGA TAT GGA TAT AC
```

RECOMBINANT MAREK'S DISEASE VIRUS

This application is a continuation-in-part of U.S. application Ser. No. 07/559,735, filed Jul. 30, 1990, now abandoned.

The present invention relates to a viral vector that is capable of expressing foreign genes, especially in chickens. In particular, this invention relates to the discovery of an insertion region of the DNA genome of Marek's disease virus ("MDV") serotype 1, into which can be inserted a heterologous nucleic acid sequence comprising a foreign gene flanked by DNA sequences from said insertion region; a plasmid comprising said nucleic acid sequence; a vaccine comprising recombinant MDV; and antiserum containing anti-recombinant MDV antibodies.

BACKGROUND OF THE INVENTION

Marek's disease is a malignant, lymphomatous disorder of chickens caused by a herpesvirus, Marek's disease virus. The virus infects chickens and results in the development of T-cell lymphomas in a variety of tissues in the weeks following infection, which ultimately results in the death or condemnation of the infected chickens at processing. The disease is unique among herpesvirus-induced disorders in that it has been controlled by the poultry industry for twenty years by vaccination of all commercial broilers and broiler breeders in the United States and many parts of the world.

MDV is a DÑA virus having an envelope and is classified in the family Herpesviridae. It is further classified into the following three serotypes:

Type I: virulent strains of MDV which are pathogenic and tumorigenic to chickens, and attenuated nonpathogenic strains derived therefrom.

Type II: naturally occurring nonpathogenic strains of MDV; and

Type III: herpesvirus of turkeys ("HVT") strains, which are nonpathogenic to chickens.

The pathogenesis of MDV infection and the classical virology of MDV have been studied throughout the twentieth century. Progress on the molecular analysis of MDV has been made during the last decade. Important advances include cloning of the viral DNA molecule (Fukuchi et al., J. Virol. 51:102-109, 1984), the generation of monoclonal antibodies against MDV; the identification of viral polypeptides; the generation of transcription maps (Schat et al, Int. J. Cancer 44:101-109, 1989), and the identification of genes on the MDV genome (Buckmaster et al, J. Gen. Virol. 69:2033-2042, 1988). To date there has been virtually no genetic analysis of the virus, although one phosphonoacetate-resistant mutant of HVT has been reported.

Marek's disease is of tremendous economic importance and effective Marek's disease vaccines are critical to the livelihood of the poultry industry. The most widely used vaccine is HVT, although currently in many regions chickens are vaccinated with a combination of MDV vaccine strains. The existing Marek's disease vaccines are unlikely to remain adequate in the future and the development of recombinant Marek's disease vaccines continues to be an important challenge to researchers in the field. Because existing Marek's disease vaccines have already been used for twenty years in the poultry industry as live herpesvirus vaccines, they are currently being researched as potential herpesvirus vectors suitable for poultry.

Virus vectors have been reported using, for example, vaccinia, papillomavirus, baculovirus, parvovirus and tobacco mosaic virus. All have been reported as a cloning vector or an expression vector for a foreign gene. MDV has also been reported as an expression vector for a foreign gene, as described by T. Ishikawa et al. in European Patent Application 0 334 530. This application describes inserting a foreign gene, such as the gene coding for hemagglutinin and neuraminidase of Newcastle disease virus ("NDV") into the gene encoding the A antigen site (gp 57-65 gene) of HVT. The recombinant HVT is used to produce a vaccine to both NDV and MDV.

In WO 88/07088, S. Martin et al. describe the method of inserting a foreign gene into a nonessential region of HVT and infecting the bird with the viral vector which will ultimately produce an immunogenic reaction to both the foreign gene product and the HVT. In particular, HVT is the only avian herpesvirus taught as a viral vector, and the nonessential regions used encode for thymidine kinase and for 1-$\beta$-D-arabinofuranosylthymine resistance.

Cochran et al., in PCT application WO 89/0140, describe insertion of foreign DNA into attenuated herpesvirus vectors. They describe a recombinant fusion protein comprising an antigenic amino acid sequence fused to a portion of the gpX glycoprotein from pseudorabies virus. A cDNA copy of the large segment of RNA of infectious bursal disease virus ("IBDV"), which encodes three polypeptides, namely VP2, VP4 and VP3, and the *E. coli* $\beta$-galactosidase gene were inserted into a nonessential site within the unique long region of the HVT genome. This recombinant virus was used as a vaccine to IBDV. MDV A antigen gene (gp 57-65) was inserted into the same site of HVT in order to produce an improved vaccine against MDV.

Although genetic analysis of some herpesvirus, including herpes simplex virus and pseudorabies, has been done, the genetic structure of the DNA genome of MDV serotype 1 ("MDV-1") is not well known.

Current vaccines against the various poultry diseases are often produced through the use of live, attenuated pathogens, which pose a risk of inoculating animals with inadequately attenuated pathogenic microorganisms.

Inactivated vaccines generally induce only a low level of immunity requiring additional immunizations. Furthermore, the neutralization-inducing antigenic determinants of the viruses may become altered by the inactivation treatment, decreasing the protective potency of the vaccine.

When more than one attenuated, live pathogen is combined in a vaccine, another problem may arise. The mutual influence of the antigenic components may result in a decrease in the immunogenicity of one or more of the constituent antigens.

In order to produce a potent vaccine to Marek's disease and at least one other avian disease, through the use of an MDV vector wherein the DNA genome of the MDV contains a foreign gene that encodes an antigen from another avian disease causing agent, a nonessential region of the MDV genome must be found and used as an insertion region. Once the foreign gene is inserted into the insertion region, the corresponding gene product must be expressed. The MDV vector will, once given to chickens, elicit an immune response to both MDV and the foreign gene product, such as a protein, preferably with a greater potency than that exhibited by a combined vaccine.

Numbers indicate nucleotide positions corresponding to the sequence shown in FIGS. 2A and 2B.

FIG. 2A, which continues on FIG. 2B, shows the DNA sequence of the MDV-1 insertion-region.

Figure 3A:
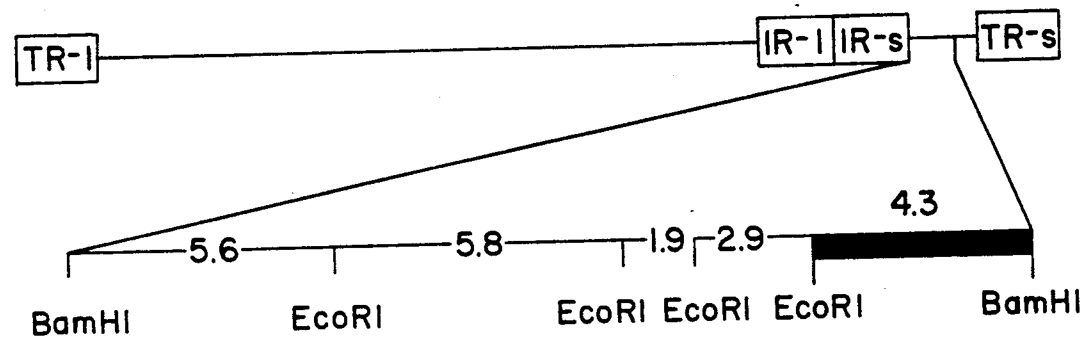
Figure 3B:
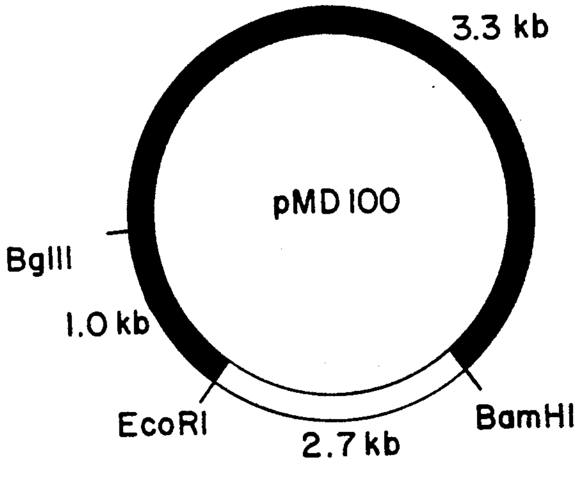

FIGS. 3A and 3B show plasmid pMD100 containing the terminal 4.3 kb EcoRI-BamHI subfragment of BamHI-A cloned into the plasmid vector pUC19.

Figure 4:
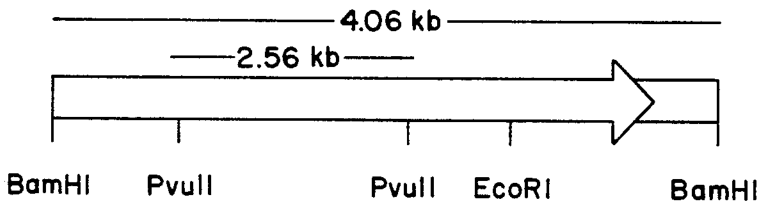

FIG. 4 shows the cassette containing the lacZ gene, which encodes β-galactosidase, expressed from the SV40 early promoter.

Figure 5A:
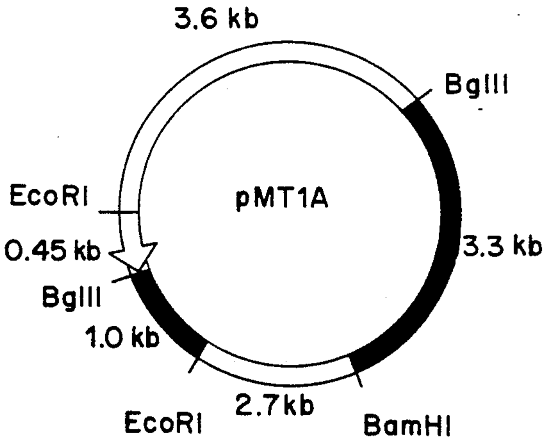
Figure 5B:
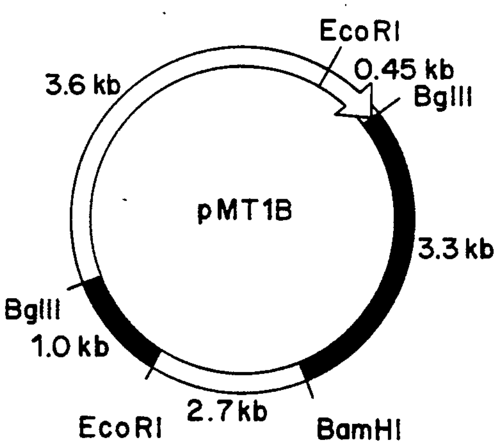

FIGS. 5A and 5B show, respectively, shows plasmids pMT1A and pMT1B containing the lacZ gene expressed from the SV40 early promoter inserted into the BglII site lying within the 4.3 kb EcoRI-BamHI subfragment of BamHI-A.

Figure 6A:
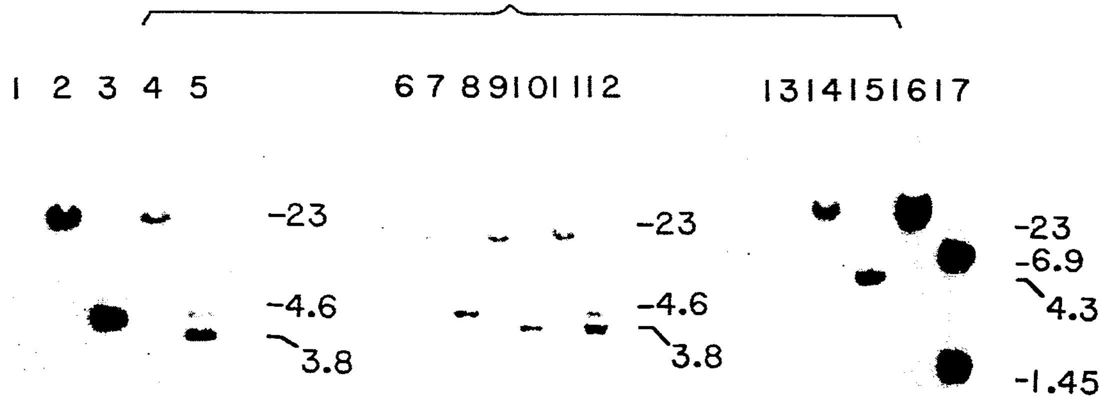
Figure 6B:
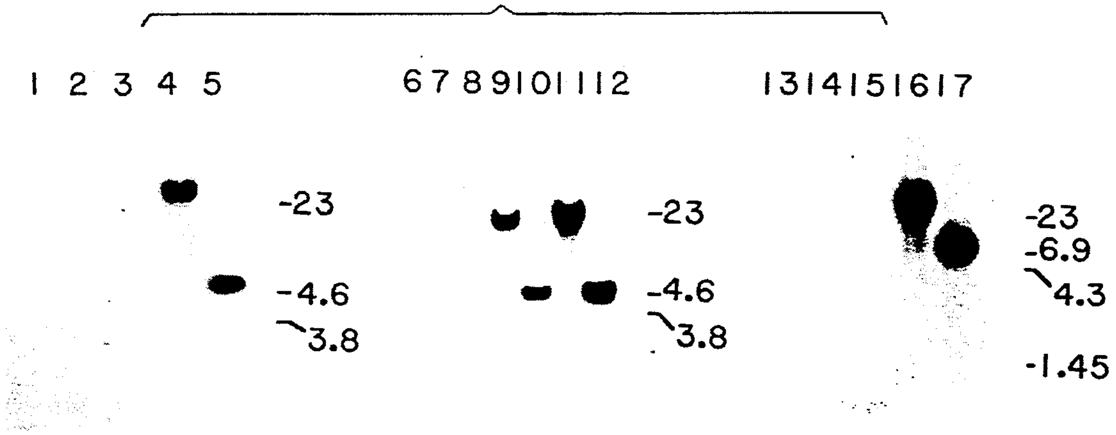

FIGS. 6A and 6B show a Southern blot analysis of the DNA from the GA parent and GAlac recombinant MDV-1 isolates indicating that the recombination event was site-specific. FIG. 6A employed a pMD100 probe and FIG. 6B, a lacZ probe.

Figure 7:
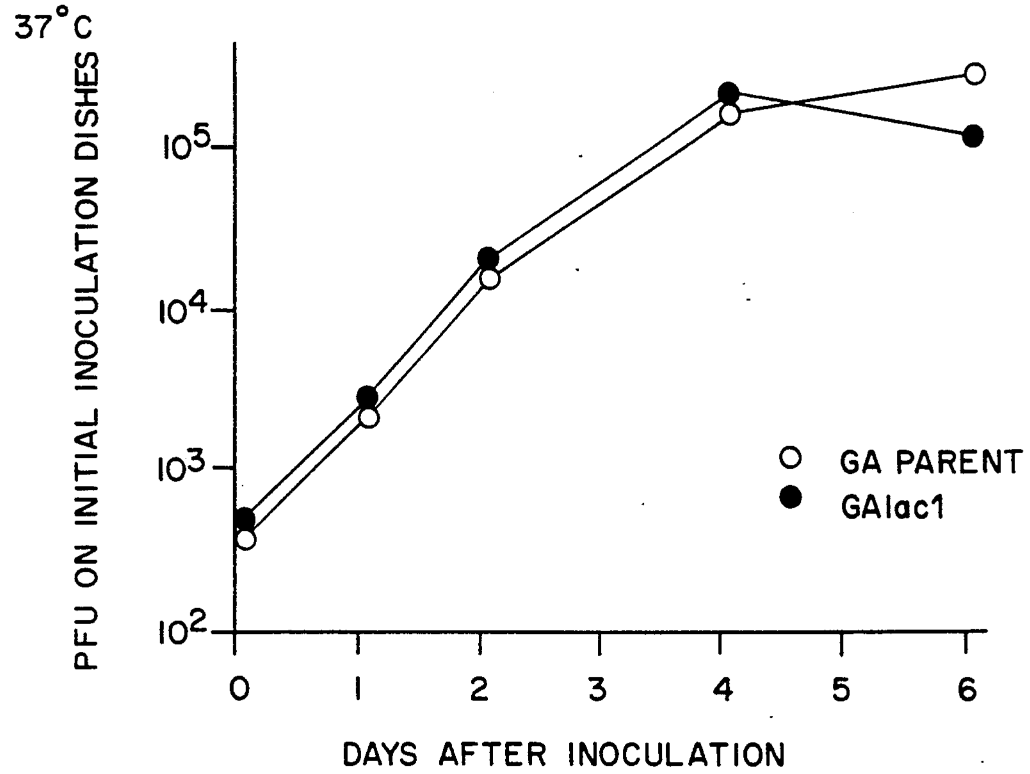

FIG. 7 shows the growth curves of parental and recombinant MDV-1 isolates at 37° C.

Figure 8:
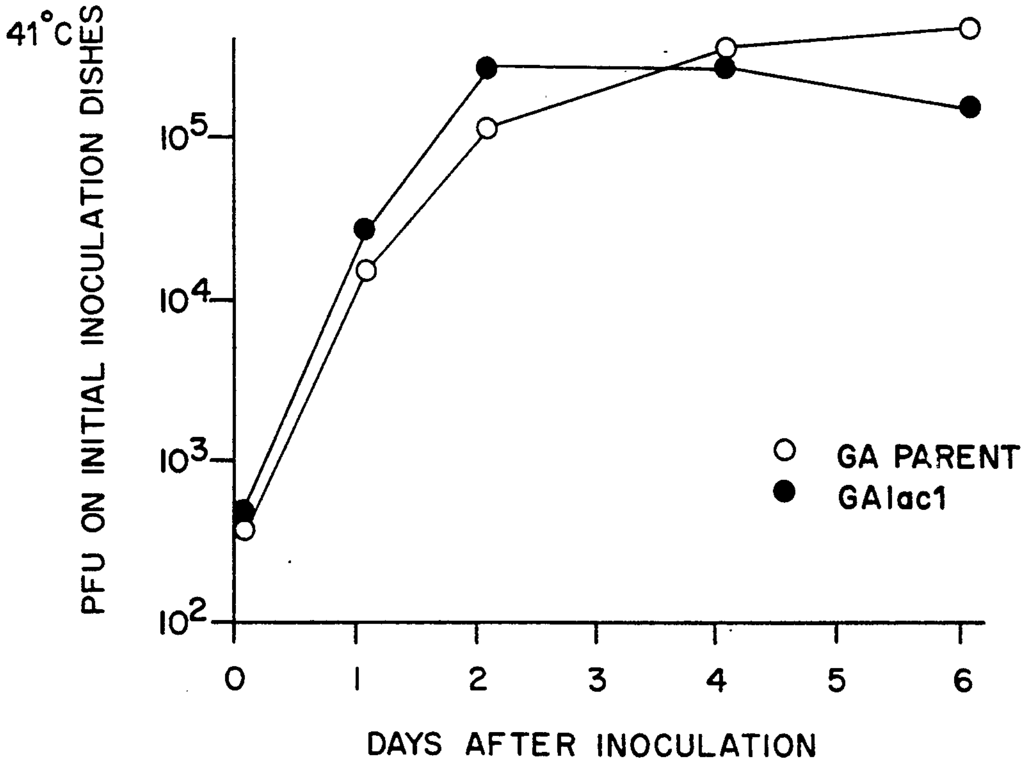

FIG. 8 shows the growth curves of parental and recombinant MDV-1 isolates at 41° C.

SUMMARY OF THE INVENTION

The present invention is the discovery of a previously unknown, nonessential insertion region on the DNA genome of MDV-1. This region comprises an open reading frame in the terminal 4.3 kb EcoRI-BamHI subfragment of BamHI-A in the unique short region of the genome. BamHI-A is the largest of 29 BamHI fragments obtained upon complete digestion of the MDV-1 genome with BamHI and BamHI-A maps to the unique short region of the genome. The region is defined by the restriction map shown in FIG. 1. This region comprises essentially the DNA sequence from nucleotide position 238 to 1050, as seen in FIG. 2. Additionally included in this invention is a plasmid comprising this insertion region.

Also included in the present invention is the recombinant MDV-1 containing a foreign gene, preferably one encoding an immunogen of another poultry disease causing agent. This recombinant virus can be used in a vaccine to protect healthy animals by eliciting an immune response to both MDV and the disease causing agent whose foreign gene was inserted into the MDV-1 genome.

It is well known that animals already infected with a specific pathogen can be treated with antiserum to that pathogen. In the present invention, the antibodies are evoked by a recombinant MDV-1 comprising a heterologous gene encoding an antigenic polypeptide derived from the specific pathogen. Antiserum directed against a recombinant MDV-1 according to the invention can be prepared by immunizing animals, for example poultry, with an effective amount of said recombinant MDV-1 in order to elicit an appropriate immune response. Thereafter the animals are bled and the antiserum can be prepared according to standard procedures.

DETAILED DESCRIPTION OF THE INVENTION

The prerequisite for a useful recombinant MDV-1 is that the heterologous nucleic acid sequence is incorporated in a nonessential position or region of the MDV-1 genome, i.e., a position or region which can be used for such incorporation without disrupting essential functions of the virus, such as those necessary for infection or replication. Such a region is called an insertion-region. The insertion-region of the present invention has not been previously described for the incorporation of heterologous DNA. Moreover, no information has been available with regard to the restriction enzyme map of the genomic region of MDV-1 used to incorporate a heterologous DNA sequence as described herein.

The preferred insertion-region, defined as the DNA sequence from nucleotide position 238 to 1050 in FIG. 2, used to incorporate a heterologous DNA sequence in order to prepare a recombinant MDV according to the invention is located in the unique short region of the genome. The insertion-region lies within the 4.3 kb EcoRI-BamHI subfragment of BamHI-A as shown in the restriction enzyme map of the genomic region containing the open reading frame in FIG. 1. Specifically, the insertion-region contains a BglII site within the 4.3 kb EcoRI-BamHI subfragment of BamHI-A, as shown in the restriction enzyme map of the genomic region containing the open reading frame in FIG. 1.

DNA sequences corresponding to the nonessential insertion-region outlined above can be used for the insertion of genes into the MDV-1 genome.

It will be understood that for the DNA sequence of the MDV-1 genome, natural variations can exist among strains. These variations may result in deletions, substitutions, insertions, inversions or additions of one or more nucleotides which possibly influence the position of one or more restriction sites, thus producing a restriction enzyme map related to the map shown in FIG. 1.

Figure 1:
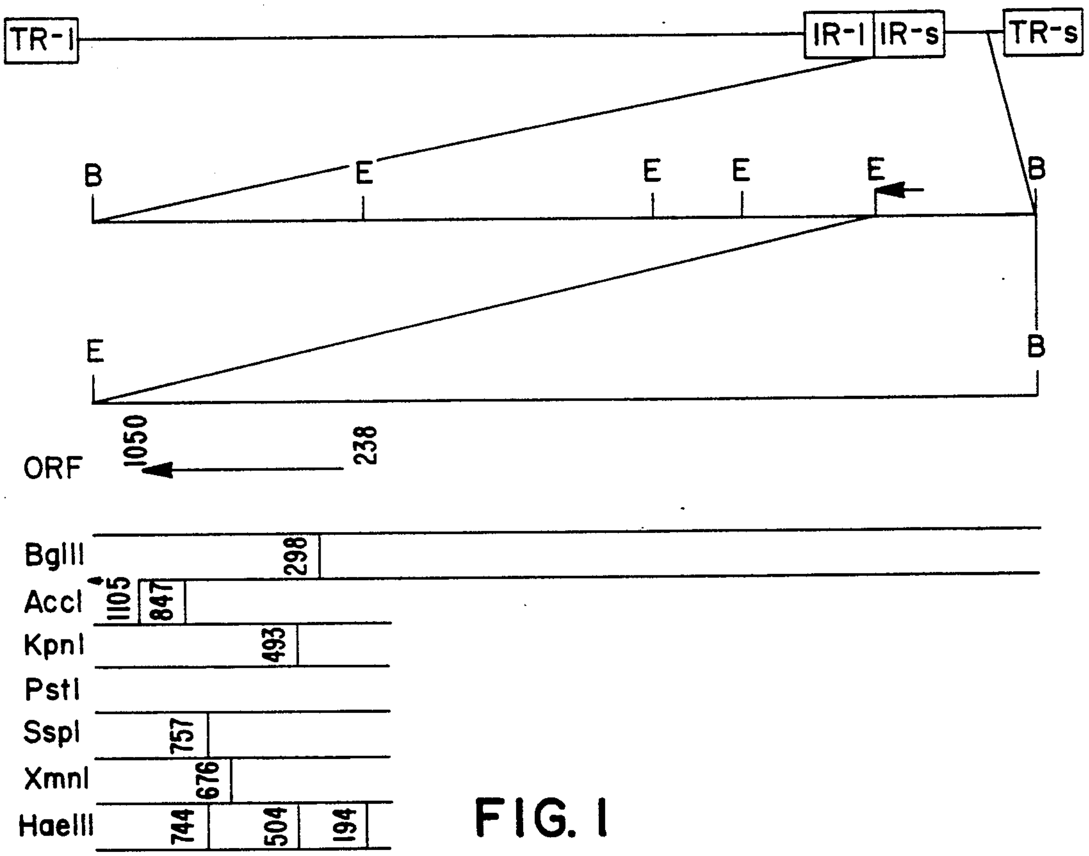
FIG. 1 shows a restriction map of the open reading frame found in the terminal 4.3 kb EcoRI-BamHI subfragment of BamHI-A in the unique short region of the DNA genome of MDV-1.

Moreover, the potential also exists to use genetic engineering technology to bring about above-mentioned variations, resulting in a DNA sequence with a restriction enzyme map related to the map shown in FIG. 1. It is intended that a recombinant MDV-1 comprising a heterologous gene incorporated into an insertion-region located within a MDV-1 genomic region characterized by any such related restriction enzyme map is also included within the scope of the present invention. Furthermore, as the insertion-region identified according to the present invention does not display essential functions, said region can be deleted partially or completely, whereafter a heterologous gene can be incorporated into said region. It is understood that a recombinant MDV-1 comprising a heterologous gene incorporated into a region of the MDV-1 genome corresponding to the insertion-region of the present invention, or a portion of this insertion-region, and characterized herein also forms part of the invention.

In summary, the insertion-region essentially defined above characterizes the localization of a region within the MDV genome which can be used to incorporate a heterologous nucleic acid sequence.

The DNA sequence of the insertion-region is shown in FIG. 2 as comprising the DNA sequence from the nucleotide position 238 to 1050. In characterizing the insertion-region of the present invention, it is important to note that natural variations may exist between MDV-1 viruses resulting in deletions, substitutions, insertions, inversions, etc. of one or more nucleotides. These variations can also be brought about by genetic engineering. Recombinant MDV-1 comprising a heterologous gene incorporated into such a related but not identical region of the MDV-1 genome also is included within the present invention. For example, a heterologous gene can be incorporated into a MDV-1 strain containing a deletion in the nucleic acid sequence of the MDV-1 genome shown in FIG. 2. The MDV-1 insertion-region defined herein by the DNA sequence shown in FIG. 2 characterizes the localization of a region within the MDV-1 genome which can be used to incorporate a heterologous nucleic acid sequence.

The heterologous nucleic acid sequence to be incorporated into the MDV-1 genome according to the present invention can be derived from any source, e.g. viral, procaryotic, eucaryotic or synthetic. Said nucleic acid sequence can be derived from a pathogen, preferably an avian pathogen, which after insertion into the MDV-1 genome can be applied to induce immunity against disease. Nucleic acid sequences derived from Infectious Bronchitis Virus ("IBV"), MDV, NDV, IBDV, Chicken Anemia Agent ("CAA"), Reovirus, Avian Retrovirus, Fowl Adenovirus, Turkey Rhinotracheitis Virus, Infectious Laryngotracheitis Virus, Eimeria species, Salmonella species, *Escherichia coli* and *Mycoplasma gallisepticum* are contemplated for incorporation into the insertion-region of the MDV-1 genome. Furthermore, nucleic acid sequences encoding polypeptides for pharmaceutical or diagnostic applications, in particular, immune modulators such as lymphokines, interferons or cytokines may be incorporated into said insertion-region.

Expression of such heterologous nucleic acid sequences requires that the sequence be linked to an adequate and functional promotor. Such a promotor can be any procaryotic, eucaryotic, viral or synthetic promotor which can direct gene expression in cells infected with MDV-1.

The recombinant MDV-1 can be prepared by a method consisting of the following steps:

- obtaining a first vector which contains the 4.3 kb BamHI-EcoRI subfragment of the BamHI-A restriction fragment of the MDV-1 genome cloned into a suitable vehicle;
- inserting at least one foreign gene sequence in the MDV-1 DNA fragment of the first vector to form a second vector;
- co-transfecting cells with DNA from the second vector and DNA from a MDV-1;
- incubating the co-transfected cells for a time sufficient for homologous recombination to occur between the DNA fragment of the second vector containing the MDV-1 DNA interrupted by the foreign gene and the genomic DNA of the attenuated MDV-1 having a homologous or similar nucleotide sequence to the MDV-1 DNA fragment of the second vector; and
- isolating from the transfected cells a recombinant virus comprising an attenuated MDV-1 and a foreign gene inserted therein.

In the first step, the 4.3 kb BamHI-EcoRI subfragment of the BamHI-A restriction fragment of the MDV-1 genome is ligated to a suitable vector to form a first vector. The vector may be derived from any suitable plasmid, cosmid, or bacteriophage, with plasmids being preferred. The most preferred plasmid is the pMD100 plasmid. The 4.3 kb BamHI-EcoRI subfragment of the BamHI-A restriction fragment is isolated by digesting a clone containing the 23 kb BamHI-A fragment of MDV-1 with BamHI and EcoRI according to customary procedures.

A clone containing the 23 kb BamHI-A fragment of MDV-1 can be isolated, if necessary, from a genomic library of MDV-1. A genomic library of the virus can be prepared by culturing MDV-1 in a host cell culture, such as an avian cell culture, according to customary procedures and isolating viral DNA from MDV-1 infected host cell culture also according to customary procedures. For example, MDV-1 is inoculated onto chicken embryo fibroblast cells and cultured to obtain virus-infected cells. The virus-infected cells are harvested, washed with buffer, centrifuged, and resuspended in Tris-hydrochloride and EDTA at a density of 1 to $5\times10^8$ cells per ml. Sodium dodecyl sulfate ("SDS") is added to a final concentration of 0.5% and proteinase K is added to a final concentration of 200 $\mu$g/ml. After incubation, additional proteinase K is added and incubation continued for 1 hour. The solution is extracted twice with a mixture of phenol-chloroform (1:1) and nucleic acids are ethanol precipitated according to customary procedures. Total DNA from infected cells is recovered by centrifugation and dissolved in 10 mM Tris-hydrochloride (pH 7.5) and 1 mM EDTA, ("TE"). The DNA is incubated with a restriction enzyme, such as Sau3A, according to the conditions recommended by the enzyme supplier. Reaction products are separated on an agarose gel and the size fraction between 16 and 20 kb is isolated. One hundred nanograms of these DNA fragments are ligated with suitable vector DNA digested with the appropriate restriction enzymes according to customary procedures. A suitable vector, for example, would be BamHI-EcoRI digested lambdaEMBL3 DNA. After ligation, the reaction mixture is packaged in vitro using commercial extracts. Recombinant bacteriophage are plated on an appropriate *E. coli* host strain such as LE392 or K802 at a density of about 100 PFU/plate. Replicas of the dishes are prepared in duplicate using nitrocellulose filters according to customary procedures. The first set of filters is hybridized according to customary procedures with radioactively labelled DNA from uninfected cells and the second set of filters is hybridized with radioactively labelled DNA from MDV-1 infected cells. After washing and exposure to X-ray film, images of the duplicate filters are superimposed in the correct orientation and several of the plaques giving a signal specifically with the probe made from MDV-1 infected cells are isolated and bacteriophages from them are amplified. These bacteriophage clones are analyzed in detail by restriction mapping of the insert to find a clone having a restriction enzyme recognition pattern indicating that it contains the BamHI-A fragment of the MDV-1 genome.

As outlined above, the 4.3 kb BamHI-EcoRI subfragment of the BamHI-A restriction fragment of the MDV-1 genome is isolated by digesting a genomic clone containing BamHI-A with BamHI and EcoRI restriction enzymes according to customary procedures. The digestion fragments are separated by electrophoresis on a low-melting point agarose gel and the 4.3 kb EcoRI-BamHI subfragment isolated and purified by standard procedures including, for example, phenol extraction and ethanol precipitation. The purified 4.3 kb EcoRI-BamHI subfragment is ligated to a suitable vector according to customary procedures using DNA ligase to generate a first vector. A preferred vector is the plasmid pUC18 or pUC19 which may be obtained from Life Technologies, Inc., P.O. Box 6009, Gaithersburg, Md. 20877. The ligation products are transformed into appropriate host cells. DNA from the transformants is purified and analyzed by customary procedures to ensure the correct first vector is obtained. The first vector contains a BglII restriction enzyme recognition site within the 4.3 kb EcoRI-BamHI subfragment. A preferred first vector is the plasmid pMD100, as seen in FIG. 3.

In the next step, at least one foreign gene sequence is inserted in the MDV-1 DNA fragment of the first vector to form a second vector.

Any foreign gene may be used for insertion into the BglII site of the first vector. The foreign gene used for inserting in the first vector may be prepared from an organism heterologous to the MDV-I. When the foreign genome is comprised of RNA, it is necessary to prepare DNA complementary to the genome by a customary method using a commercially available reverse transcriptase. For the proper insertion of the foreign gene in the first vector, it is preferred to prepare the restriction map of the foreign gene and determine the nucleotide sequence of the foreign gene. The preparation of the restriction map and determination of the nucleotide sequence can be conducted using customary procedures.

For expressing the foreign gene, it is necessary that an adequate and functional promoter be linked to the foreign gene. The promoter can be any eucaryotic, procaryotic, or viral promoter capable of directing gene transcription cells infected with the recombinant MDV-1. Examples include promoters derived from the retroviral long terminal repeat, SV40 promoters, or promoters present in the genomes of MDV or HVT.

The insertion of the foreign gene in the first vector may be conducted by customary procedures. The first vector is cleaved at the BglII site which lies within the 4.3 kb EcoRI-BamHI subfragment of the BamHI-A restriction fragment of the MDV-1 genome. The foreign gene is ligated in the BglII site using DNA ligase and customary procedures to form a second vector. The ligation products are transformed into appropriate host cells. Transformants are purified and analyzed by customary procedures to ensure that the correct second vector is obtained. Plasmid DNA from the second vector is prepared and banded twice by cesium chloride equilibrium centrifugation using customary procedures.

In the third step, cells are co-transfected with DNA from the second vector obtained as outlined above and with DNA from a MDV-1 strain. It should also be possible to transfect cells infected with MDV-1 with DNA from the second vector.

DNA from a MDV-1 is obtained by infecting secondary chicken embryo fibroblasts cultures with an appropriate attenuated MDV-1 and incubating the cultures until extensive cytopathic effects are evident, according to customary procedures. Total cellular DNA is purified by incubating the MDV-1 infected cells in digestion solution containing 0.2 mg/ml proteinase K, 0.5% SDS, 100 mM sodium chloride, 10 mM Tris-hydrochloride (pH 8), and 1 mM EDTA for 4 hours. The solution is extracted once with phenol and twice with chloroform-isoamyl alcohol (24:1). The DNA is precipitated by the addition of 2 volumes of absolute ethanol, recovered by centrifugation, dissolved in TE, and quantitated by extinction at 260 nm. DNA prepared in this manner is hereinafter referred to as "MDV DNA". MDV DNA can be prepared from cultures infected with any suitable MDV-1.

Co-transfection of DNA from the second vector with MDV DNA is done according to customary procedures for calcium phosphate-mediated transfection (F. L. Graham et al., Virology 52:456–467, 1977; and N. D. Stow et al., J. Gen. Virol. 33:447–458, 1976) with the following modifications. Primary chicken embryo fibroblasts are prepared from ten day old chicken embryos obtained from specific-pathogen-free eggs. One day later, secondary chicken embryo fibroblasts are prepared from the primary cultures. While the secondary chicken embryo fibroblasts are being prepared, calcium phosphate/DNA precipitates are made, the tubes are allowed to sit until a fine precipitate is visible, and the contents are then split equally between two dishes of freshly plated cells. Following incubation, the cultures are rinsed in maintenance medium lacking serum, treated for 3 minutes with 15% glycerol in 1×HBSP (0.75 mM $Na_2HPO_4.7H_2O$, 5 mM KCl, 140 mM NaCl, 6 mM glucose, 25 mM HEPES, pH 7), rinsed, and fed with complete maintenance medium.

In the fourth step, the co-transfected cells are incubated for a time sufficient for homologous recombination to occur between the DNA fragment of the second vector containing the DNA fragment of the MDV-1 genome together with the foreign gene, and a portion of the DNA of the attenuated MDV-1 having a homologous or similar nucleotide sequence to the MDV-1 DNA fragment in the second vector.

Finally, a recombinant virus comprising an attenuated MDV-1 and a foreign gene inserted therein is isolated from the cultured transfected cells and recombinants containing other foreign genes may be identified by several methods including hybridization with an appropriate probe, reactivity with a specific antibody, and loss or gain of a relevant enzyme activity.

For example, to identify a recombinant virus using hybridization, the maintenance medium from the cultures is discarded and fresh maintenance medium containing agarose is overlaid on the cells. Cultures are incubated for 1 to 3 days until plaques begin to form. A portion of each plaque is collected together with a portion of agarose gel and transferred onto a commercially available membrane filter. The filter is subjected to denaturation and neutralization and the DNA from each plaque is immobilized on the filter according to customary procedures. The resultant filter is subjected to plaque hybridization according to customary procedures using a radioactively labelled probe consisting of the foreign gene. Plaques which hybridize to the probe are regarded as positive. The recombinant plaques corresponding to the positive hybridization signals are isolated from the agarose overlay on the tissue culture dish and propagated according to customary procedures for MDV-1.

Other methods may be used to detect the presence of a foreign gene in the transfectants. For example, the tissue culture dishes containing recombinant MDV-1 plaques may be stained using antibody specific for the foreign gene product. Plaques which contain recombinant MDV-1 producing the foreign gene product will be specifically recognized by the antibody.

The recombinant MDV-1 is propagated in cultured cells as outlined above. Total DNA is isolated from recombinant MDV-1 infected cells and subject to Southern blot analysis using customary procedures to ensure that the foreign gene has been inserted in the targeted site; namely, the 4.3 kb EcoRI-BamHI subfragment of BamHI-A.

A live, recombinant MDV-1 expressing one or more different heterologous polypeptides of avian pathogens can be used to vaccinate animals, particularly avian species such as chickens and turkeys susceptible to these pathogens. Vaccination with a live vector vaccine prepared from the recombinant MDV-1 as described herein is preferably followed by replication of the recombinant MDV-1 which expresses in vivo the heterologous polypeptide and the MDV-1 polypeptides, in the inoculated host. If a protective immune response is elicited, the animal so inoculated will then be protected from subsequent infection by those pathogens.

A recombinant MDV-1 of the present invention containing and expressing one or more different heterologous polypeptides can serve as a monovalent or multivalent vaccine. Such a MDV-1 can also be used to prepare an inactivated vaccine. These vaccines can be prepared by methods well known to those skilled in the art of the preparation of vaccines.

The examples are given to further explain, but not limit, the invention.

EXAMPLE 1 — MATERIALS

The GA strain of MDV-1 was obtained from M. Nonoyama, Showa Research Institute for Biomedicine, St. Petersburg, Fla. This strain was used to make the BamHI plasmid library of MDV-1 (Fukuchi et al., 1984). The strain was passaged in secondary chicken embryo fibroblasts ("CEF") until approximately passage level 75 was obtained.

EXAMPLE 2 — PLASMID CONSTRUCTION

Cloning procedures were done using standard methods. Restriction enzyme digestions were done according to the recommendations of the manufacturers. Plasmid pMD100 contains the terminal 4.3 kb EcoRI-BamHI subfragment of BamHI-A cloned into the plasmid vector pUC19 as seen in FIG. 3. The 4.3 kb EcoRI-BamHI subfragment lies entirely within the unique short region of the genome. A lacZ cassette was obtained from Intervet International, Boxmeer, The Netherlands. The cassette was constructed by removing the lacZ gene from the eukaryotic assay vector pCH110 (Pharmacia, Inc., Piscataway, N.J.) and modifying the gene as follows: the 72 base pair Sph1 fragment near the SV40 origin of replication was replaced with a double stranded synthetic oligonucleotide having the following structure:

5' - GGATCCGTCGACCATG - 3'

3' - GTACCCTAGGCAGCTG - 5'

Insertion of the linker between the two Sph1 restriction sites of pCH110 did not restore the recognition sequence for Sph1 on either site and created both a BamHI and a SalI site upstream of the SV40 early promoter. Subsequent digestion of this construct with BamHI generated a 4.0 kb expression cassette. The lacZ gene is 4056 bp in length and is under control of the SV40 early promoter, as seen in FIG. 4.

To insert the lacZ cassette into pMD100, one microgram of pMD100 was digested with BglII (Bethesda Research Laboratories [BRL], Gaithersburg, Md.). Approximately one unit of calf intestinal alkaline phosphatase (Boehringer Mannheim, Indianapolis, Ind.) was added and the incubation continued for 30 minutes. The reaction conditions were adjusted to 20 mM Tris-hydrochloride (pH 7.4), 5 mM EDTA, 0.5% sodium dodecyl sulfate (SDS), and 100 μg/ml proteinase K (BRL) and the incubation continued for an additional hour. The reaction was extracted once with phenol, sodium acetate was added to a final concentration of 0.1M, and two volumes of absolute ethanol were added. The DNA was collected by centrifugation for 15 minutes at top speed in a microfuge. The DNA pellet was dissolved in 20 μl of 10 mM Tris-hydrochloride (pH 7.4), 1 mM EDTA (TE).

The modified lacZ gene was inserted into the BglII site of pMD100 by the following ligation reaction. Fifty nanograms of BglII-digested pMD100 and 10 ng of the lacZ cassette were incubated overnight at 4° C. with 2 units of T4 DNA ligase (BRL) in a total volume of 10 μl of ligation buffer consisting of 66 mM Tris-hydrochloride (pH 7.6), 6 mM $MgCl_2$, and 1 mM ATP. The ligation reaction was diluted in TE to a concentration of 1 ng vector per μl, and 2 μl of the diluted reaction was used to transform DH5α competent cells. Plasmid DNA was purified from individual colonies and analyzed for the presence of lacZ sequences. The lacZ-containing pMD100 was designated pMT1A, as shown in FIG. 5. A second plasmid, pMT1B, also in FIG. 5, was constructed which differs from pMT1A in the orientation of the lacZ cassette. Plasmid DNAs were prepared by standard procedures and banded twice by cesium chloride equilibrium centrifugation.

EXAMPLE 3 — MDV DNA PREPARATION

Total DNA from MDV-infected CEF was prepared as described above. Briefly, secondary CEF growing in 75 $cm^2$ flasks ($1.6\times10^7$ cells plated/flask) were infected with cell-associated virus ($10^5$ PFU/flask) and incubated for six days. DNA was purified by incubating the cells in digestion solution containing 0.2 mg/ml proteinase K (BRL), 0.5% SDS, 100 mM NaCl, 10 mM Tris-hydrochloride (pH 8), and 1 mM EDTA for 4 hours. The solution was extracted once with phenol and twice with chloroform-isoamyl alcohol (24:1). The DNA was precipitated by the addition of 2 volumes of absolute ethanol, recovered by centrifugation, dissolved in TE, and quantitated by extinction at 260 nm. DNA prepared in this manner will be referred to as MDV DNA.

EXAMPLE 4 — TRANSFECTIONS

A dose response for plaque formation by MDV DNA was determined for each MDV DNA preparation and an amount of MDV DNA giving maximum plaque yields was used for co-transfections. Prior to transfection, 4 to 8 μg of MDV DNA and 0.5 μg plasmid DNA were ethanol precipitated, recovered by centrifugation, and dissolved in 50 μl TE.

Primary chicken embryo fibroblasts were prepared from 10 day old chicken embryos obtained from specific-pathogen-free eggs. The cells were suspended at a concentration of $8\times10^5$ cells/ml and plated at a density of $1.6\times10^7$ cells/75 $cm^2$ flask (20 ml/flask). One day later, primary cultures were washed once in maintenance medium lacking serum and removed from flasks by exposure to 0.05% trypsin. The trypsin was inactivated by the addition of approximately 0.5 ml of calf serum and the cells were centrifuged at 2500 rpm for 10 minutes, resuspended in 1.5 times the original volume and plated as primary cultures with a concentration of approximately $8\times10^5$ cells/ml, and filtered twice through cheesecloth. The cells were plated in 60 mm gridded tissue culture dishes at a density of $4\times10^6$ cells/dish (5 ml/dish) immediately before adding the calcium phosphate/DNA precipitates.

While the secondary chicken embryo fibroblasts were being prepared, the calcium phosphate/DNA precipitates were made by the successive addition of the following reagents to 15 ml polystyrene tubes: 388 microliters water, 50 microliters of the DNA in TE, and 62 microliters of 2M calcium chloride. Exactly 500 microliters of 2×HBSP (2×HBSP=1.5 mM $Na_2HPO_4.7H_2O$, 10 mM KCl, 280 mM NaCl, 12 mM glucose, 50 mM HEPES, pH 7) was slowly added and the contents of the tube were mixed by gently blowing 5-6 bubbles from the tip of a pipet into the solution. The tubes were allowed to sit for 30 minutes at ambient temperature until a fine precipitate was visible, gently mixed, and split equally between two dishes of freshly plated cells. Following a 4 hour incubation at 37° C., the cultures were carefully rinsed in maintenance medium without serum, treated for 3 minutes with 15% glycerol in 1×HBSP (1.5 ml/dish), rinsed, and fed with complete maintenance medium.

Plaques were counted six days later. The frequency of plaque formation for the co-transfection experiments varied depending on the MDV DNA preparation used, as shown in Table 1.

isolated plaques were titered on freshly plated secondary CEF. Seven days later, the dishes were stained and blue plaques were picked and replated.

Upon staining, 0.3–1.0% of the plaques counted were positive for β-galactosidase activity, as shown in Table 1 above. Each positive plaque was subjected to approximately four cycles of picking and staining in order to obtain a stable, plaque-purified isolate. Stable, plaque-purified isolates were obtained for 18% of the blue plaques initially picked, and thus, stable recombinant isolates were derived from approximately 0.1% of the original plaques present on the transfection dishes. Once a stable recombinant was isolated, plaques derived from it remained 100% β-galactosidase-positive after either passage of the virus in cell culture or re-transfection of the viral DNA into secondary CEF. A total of four recombinant viruses expressing lacZ were isolated. These isolates were designated GAlac1, GAlac2, GAlac3, and GAlac4. Three of the isolates (GAlac1, GAlac2, and GAlac3) were made using pMT1B and one (GAlac4) was made using pMT1A.

EXAMPLE 6 — ANALYSIS OF GAlac RECOMBINANT DNA

Secondary CEF growing in 75 $cm^2$ flasks were infected with purified GAlac recombinants to yield approximately 10,000 plaques/flask. Total DNA from cultures infected with recombinant virus was purified as described above. Southern blots were prepared using standard procedures and probed with either the 4.3 kb insert from pMD100, a 2.5 kb PvuII fragment of pCH110 containing the 5' end of the lacZ gene, or pBR322 as shown in FIG. 6. Probes were radiolabelled with $^{32}P$-deoxynucleotides using a random primed DNA synthesis kit (Boehringer Mannheim, Indianapolis, Ind.). DNA-DNA hybridizations were done at 42° C. for 16 hours in 50% formamide, 10 mM Tris-hydrochloride (pH 7.5), 0.1% SDS, 100 μg/ml denatured salmon sperm DNA, 5×Denhardt's solution contained 0.1% Ficoll 400 (Sigma Chemical Company, St. Louis, Mo. U.S.A.), 0.1% polyvinylpyrrolidone, and 6×SSC (1×SSC contains 0.15M sodium chloride and 0.015M sodium citrate [pH 7]). Hybridized nitrocellulose filters were washed 4 times for 30 minutes each at 65° C. in wash solution consisting of 0.1×SSC and 0.1% SDS.

TABLE 1

Summary of co-transfection attempts to generate GAlac recombinants.

| MDV DNA[a] (μg) | Plasmid[b] | Plaques/[c] precipitate | Total plaques obtained | β-gal positive plaques | Frequency β-gal positives (%) | Stable β-gal[d] positives (designation) | Frequency stable β-gal positives (%) |
|---|---|---|---|---|---|---|---|
| 4.5 | pMT1B | 323 | 712 | 7 | 1 | 1 (GAlac1) | 0.1 |
| 4.5 | pMT1B | 389 | | | | | |
| 6 | pMT1B | 159 | 498 | 3 | 0.6 | 1 (GAlac2) | 0.2 |
| 6 | pMT1B | 116 | | | | | |
| 6 | pMT1B | 223 | | | | | |
| 8 | pMT1B | 306 | 1450 | 9 | 0.6 | 1 (GAlac3) | 0.07 |
| 8 | pMT1B | 411 | | | | | |
| 8 | pMT1B | 360 | | | | | |
| 8 | pMT1B | 373 | | | | | |
| 8 | pMT1A | 600 | 915 | 3 | 0.3 | 1 (GAlac4) | 0.1 |
| 8 | pMT1A | 315 | | | | | |

[a]Total DNA from GA-infected CEF was prepared as outlined in Materials and Methods.
[b]500 ng plasmid DNA was co-precipitated with MDV DNA.
[c]Each calcium phosphate precipitate was split equally between two 60 mm gridded dishes. Numbers are sums of plaques present per precipitate.
[d]Number of plaque purified isolates which were 100% β-galactosidase positive.

The number of plaques obtained after three transfection experiments averaged 296±96 and ranged from 116 to 411 plaques per precipitate. Thus, for optimum co-transfections, each MDV DNA preparation should be characterized in terms of its transfection efficiency.

EXAMPLE 5 — DETECTION AND ISOLATION OF STABLE GAlac RECOMBINANTS

Recombinants containing the lacZ gene of E. *coli* were identified as follows. Seven days after the transfection, the tissue culture medium was reduced to 2 mls and 20 μl of a Bluo-gal (BRL) solution (20 mg/ml, freshly prepared in dimethyl sulfoxide) was added to the dishes, resulting in a final Bluo-gal concentration of 0.2 mg/ml. The dishes were incubated in the tissue culture incubator for 1-2 hours. Blue plaques were picked as they appeared and suspended in 0.05% trypsin to disaggregate the cells. After 5 minutes, 1-2 drops of calf serum were added to inactivate the trypsin, and the DNA sequencing of RNA-free plasmids was done using the dideoxy sequencing method and Sequenase I (United States Biochemical Corporation, Cleveland, Ohio). Sequences were analyzed using the commercial software package "Microgenie" (Beckman Instruments, Inc., Palo Alto, Calif.).

EXAMPLE 7 — SOUTHERN ANALYSIS ON GAlac RECOMBINANTS

To examine whether the recombination occurred in a site-specific manner within the 4.3 kb EcoRI-BamHI subfragment of BamHI-A, DNA from the recombinant viruses was subjected to Southern blot analysis, as seen in FIG. 6. In Panel A, the blots were probed with the 4.3 kb EcoRI-BamHI subfragment of BamHI-A which was obtained from pMD100. In Panel B, the probe used was the 2.5 kb PvuII fragment lying within the lacZ gene. For each sample, 10 $\mu$g DNA was digested with BamHI or with a combination of BamHI and EcoRI. Lanes 1, 6, 13 - CEF DNA cut with BamHI; lanes 2, 7, 14 - DNA from CEF infected with the parent GA strain cut with BamHI; lanes 3, 8, 15 - DNA from CEF infected with the parent GA strain cut with BamHI and EcoRI; lanes 4, 9, 11, 16 - DNA from CEF infected with GAlac1, 2, 3, or 4, respectively, cut with BamHI; lanes 5, 10, 12, 17 - DNA from CEF infected with GAlac1, 2, 3, or 4, respectively, cut with BamHI or EcoRI. In all cases, recombination occurred at the targeted site. The 4.3 kb insert of pMD100 hybridized to a 4.6 and a 3.8 kb EcoRI-BamHI band of GAlac1, GAlac2 and GAlac3, indicating that the parental 4.3 kb band was modified by the addition of 4 kb of DNA containing one EcoRI site. The lacZ probe hybridized to a 4.6 kb band in these recombinants, indicating that the 4.6 kb band contained lacZ sequences. The 3.8 kb band was not detected by the lacZ probe because the 2.5 kb PvuII probe used was homologous to the 5' end of the lacZ gene and did not extend beyond the EcoRI site within the lacZ gene. Hybridization of the same probes to GAlac4 indicated that the recombination event occurred similarly; however, the lacZ gene was positioned in the opposite orientation in the virus (FIG. 6).

Recombination of lacZ into the MDV genome could have occurred in two ways. A double crossover event, involving both flanks of the lacZ gene in pMD100 would have resulted in replacement of the 4.3 kb EcoRI-BamHI subfragment of BamHI-A with the lacZ-containing derivative. Single crossover events in either of the flanks of the lacZ gene would have resulted in a derivative virus containing all the parental sequences plus pMT1A or pMT1B in is entirety, including pUC19 sequences.

Results from the Southern blot analysis indicate that recombination occurred by a double crossover event. First, if pUC19 sequences had been inserted into MDV by a single crossover event, it would have been expected that the 4.3 kb insert of pMD100 would hybridize to three fragments of sizes 4.6, 4.3, and 3.8 kb in the cases of GAlac1, 2, and 3, and three fragments of sizes 6.9, 4.3, and 1.5 in the case of GAlac4. The fact that the pMD100-derived probe did not detect a 4.3 kb band provides evidence that pUC19 sequences were not recombined into the MDV recombinants. Second, pBR322, which shares DNA sequences with pUC19, failed to hybridize to DNA from any of the recombinants, indicating that pUC19 sequences did not recombine into the virus.

EXAMPLE 8 — SEQUENCE OF THE INSERTION-SITE

Insertion of lacZ into the BglII site of the 4.3 kb EcoRI-BamHI subfragment of BamHI-A indicated that this site is nonessential for virus replication in cell culture. Sequencing data from both directions surrounding the relevant BglII site was undertaken to identify any genes that might have been disrupted, as seen in FIG. 2. Insertion into the BglII site would have disrupted a leftward open reading frame 810 base pairs long and a rightward open reading frame 462 base pairs long.

EXAMPLE 9 — GROWTH CURVES ON PARENTAL AND RECOMBINANT MDV ISOLATES

Primary CEF were prepared and plated in 75 $cm^2$ flasks. Primary cultures were harvested and replated as secondary cultures on days 0, 1, 2, 4, and 6, as needed. On day 0, twelve 60 mm dishes of secondary CEF were inoculated with approximately 300 PFU of the parental MDV strain and twelve dishes were inoculated with approximately 300 PFU of the GAlac1 recombinant. Plaques present on two of the dishes for each strain were counted six days after inoculation to determine the actual number of PFU plated. On days 0, 1, 2, 4, and 6, duplicate inoculation dishes were harvested and virus present was titered onto freshly prepared secondary CEF. Six days after titering, plaques were counted and the number of PFU present on the original inoculation dishes determined.

Over a six day period, there was no detectable difference in the growth properties of the two strains in secondary CEF at either 37° C. or 41° C., as seen in FIGS. 7 and 8. Both strains did grow faster at 41° C. than at 37° C.; however, the final yield of virus obtained per dish was the same at both temperatures.

EXAMPLE 10 — IN VIVO ANALYSIS OF PARENTAL AND RECOMBINANT MDV ISOLATES.

Day-old specific-pathogen free, single comb white leghorn chickens were wing-banded and inoculated intraabdominally with cells infected with the parental MDV strain, cells infected with the GAlac1 recombinant, or uninfected cells. One week post inoculation (PI), plasma samples from each bird were obtained. Spleen cells were isolated from each group, counted, and equivalent numbers of viable cells ($5\times10^7$ and $5\times10^6$) were cocultivated onto freshly prepared CEF. Lymphocytes were purified by centrifugation through "Histopaque 1077" (Sigma Chemical Co., St. Louis, Mo.), counted, and equivalent numbers of viable cells ($1\times10^7$ and $1\times10^6$) were cocultivated onto freshly prepared CEF. Six days later, plaques on the cocultivation dishes were counted. The results of these titrations are shown in Table 2 for spleen cells and in Table 3 for lymphocytes.

TABLE 2

Virus reisolations from spleens

| Strain | Dose (PFU) | Plaques obtained (# of cells plated) $5\times10^7$ | $5\times10^6$ | Average plaques obtained (# of cells plated) $5\times10^7$ | $5\times10^6$ |
|---|---|---|---|---|---|
| Parent | 216 | 54, 60 | 12, 19 | 57 | 16 |
| | 390 | 17, 18 | 2, 5 | 18 | 4 |
| | 682 | 4, 3 | 1, 0 | 4 | 1 |
| GAlac | 526 | 30, 20 | 1, 6 | 25 | 4 |

TABLE 2-continued

| Virus reisolations from spleens | | | | | |
|---|---|---|---|---|---|
| | Dose | Plaques obtained (# of cells plated) | | Average plaques obtained (# of cells plated) | |
| Strain | (PFU) | $5 \times 10^7$ | $5 \times 10^6$ | $5 \times 10^7$ | $5 \times 10^6$ |
| | 914 | 32, 47 | 6, 2 | 40 | 4 |
| | 1554 | 62, 68 | 4, 7 | 65 | 5 |
| | — | 0, 0 | 0, 0 | 0 | 0 |

TABLE 3

| Virus reisolations from lymphocytes | | | | | |
|---|---|---|---|---|---|
| | Dose | Plaques obtained (# of cells plated) | | Average plaques obtained (# of cells plated) | |
| Strain | (PFU) | $1 \times 10^7$ | $1 \times 10^6$ | $1 \times 10^7$ | $1 \times 10^6$ |
| Parent | 216 | 9, 9 | 1, 1 | 9 | 1 |
| | 390 | 9, 4 | 0, 0 | 7 | 0 |
| | 682 | 1, 4 | 1, 0 | 3 | 1 |
| GAlac | 526 | 19, 35 | 2, 7 | 27 | 5 |
| | 914 | 79, 93 | 9, 16 | 86 | 13 |
| | 1554 | 128, 142 | 11, 18 | 135 | 15 |
| | — | 0, 0 | 0, 0 | 0 | 0 |

These results show that recombinant MDV containing a $\beta$-galactosidase gene inserted into the BglII site of the 4.3 kb EcoRI-BamHI subfragment of BamHI-A can be reisolated from spleen cells and can induce viremia in chickens in a manner similar to the parent MDV strain. Some of the titration dishes were stained for $\beta$-galactosidase activity using Bluogal as the substrate to assess the stability of the GAlac recombinant after it had been passed through chickens. Of 473 plaques stained from the GAlac titrations, all were positive for $\beta$-galactosidase activity. At 3 and 6 weeks PI, plasma samples were again obtained, and lymphocytes were purified and assayed for the presence of MDV to assess the duration of viremia for each strain. Both viruses persisted in lymphocytes for at least six weeks PI, although the viremias decreased significantly by the 3-week observation point. Antibody responses to MDV were assayed on all individual plasma samples from weeks 1, 3, and 6 PI by an indirect immunofluorescence assay. An anti-MDV antibody response was observed in all groups injected with either the parent virus or the GAlac recombinant. The antibody response appeared at the 3-week sampling time and increased in strength at the 6-week sampling time.

From these experiments, it can be concluded that the BglII site lying within the 4.3 kb EcoRI-BamHI subfragment of BamHI-A can be used for stable integration of foreign sequences without significant effect on essential MDV functions required for infection and replication. Furthermore, it can be concluded that the ability of the virus to elicit an anti-MDV immune response is not impaired by integration of foreign sequences into the insertion site.

I claim:

1. An insertion region of the DNA genome of Marek's disease virus serotype 1 ("MDV-1") that when used to construct recombinant MDV, does not affect the viability of said MDV-1 consisting essentially of an open reading frame in the terminal 4.3 kb EcoRI-BamHI subfragment of BamHI-A in the unique short region of the genome, having a restriction enzyme site map essentially as illustrated by FIG. 1.

2. An insertion region according to claim 1 comprising the DNA sequence from nucleotide position 238 to 1050 as illustrated in FIG. 2.

3. An insertion region according to claim 2 wherein said region comprises an insertion site containing the recognition sequence for the BglII restriction enzyme.

4. A plasmid comprising the insertion region according to claim 1.

5. A plasmid according to claim 4, wherein the plasmid is pMD100.

6. A plasmid according to claim 4, wherein a foreign gene derived from poultry disease causing agent is inserted into said insertion region.

7. A plasmid according to claim 6, wherein said foreign gene is under control of a promoter capable of driving expression of said sequence.

8. A plasmid according to claim 7, wherein the said promoter is SV40 early promoter.

9. A host cell transformed with a plasmid according to claim 4.

10. A recombinant MDV-1 comprising the genomic DNA of MDV-1 and at least one foreign gene derived from a poultry disease causing agent, wherein said foreign gene is inserted into said genomic DNA in the insertion region according to claim 1.

11. A recombinant MDV-1 according to claim 10 comprising a promoter for the insertion region, which promoter is functional in a host cell for expressing said foreign gene.

12. A recombinant MDV-1 according to claim 10, wherein said foreign gene is incorporated in the BglII restriction site of the 4.3 kb EcoRI-BamHI subfragment of BamHI-A.

13. A recombinant MDV-1 according to claim 11, wherein at least one polypeptide encoded by said foreign gene and at least one polypeptide encoded by said genomic DNA of the MDV-1 is expressed.

* * * * *